(12) United States Patent
Hayakawa et al.

(10) Patent No.: US 7,112,611 B2
(45) Date of Patent: Sep. 26, 2006

(54) 1G(α)-AMINO-N-HYDROXY-ACETAMIDE DERIVATIVES

(75) Inventors: Kenji Hayakawa, Takarazuka (JP); Genji Iwasaki, Tsukuba (JP); Shinichi Koizumi, Ibaraki (JP); Ichiro Umemura, Ibaraki (JP)

(73) Assignee: Novartis AG, Basel (CH)

( * ) Notice: Subject to any disclaimer, the term of this patent is extended or adjusted under 35 U.S.C. 154(b) by 301 days.

(21) Appl. No.: 10/467,611

(22) PCT Filed: Feb. 8, 2002

(86) PCT No.: PCT/EP02/01345

§ 371 (c)(1),
(2), (4) Date: Aug. 7, 2003

(87) PCT Pub. No.: WO02/064552

PCT Pub. Date: Aug. 22, 2002

(65) Prior Publication Data

US 2004/0082630 A1  Apr. 29, 2004

(30) Foreign Application Priority Data

Feb. 9, 2001 (GB) ................................ 0103303.4

(51) Int. Cl.
*A61K 31/18* (2006.01)
*C07C 303/00* (2006.01)

(52) U.S. Cl. ............................ 514/602; 564/80; 564/84

(58) Field of Classification Search ................ 514/415, 514/602; 548/255; 564/84, 80
See application file for complete search history.

(56) References Cited

U.S. PATENT DOCUMENTS

| 2,513,826 | A |   | 7/1950  | Sprung et al. |         |
|-----------|---|---|---------|---------------|---------|
| 4,806,528 | A |   | 2/1989  | Hanreich      |         |
| 5,338,755 | A |   | 8/1994  | Wagnon et al. |         |
| 5,455,258 | A | * | 10/1995 | MacPherson et al. | 514/357 |
| 5,500,337 | A |   | 3/1996  | Benard et al. |         |
| 5,663,431 | A |   | 9/1997  | Di Malta et al. |       |
| 5,932,695 | A |   | 8/1999  | Floyd et al.  |         |
| 6,150,394 | A | * | 11/2000 | Watanabe et al. | 514/415 |

FOREIGN PATENT DOCUMENTS

| EP | 308860 | 3/1989 |
| EP | 915086 | 5/1999 |
| EP | 0 950 656 | 10/1999 |
| JP | 11-236369 | 8/1999 |
| WO | 96 00214 | 1/1996 |
| WO | 9833768 | 8/1998 |
| WO | 99 06340 | 2/1999 |
| WO | 00 44709 | 8/2000 |
| WO | 00 44713 | 8/2000 |
| WO | WO 01/10827 | 2/2001 |

OTHER PUBLICATIONS

US Appl. No. #10/048,932.*
Casini, et al., "Sulfonamides and sulfonylated derivatives as anti-cancer agents," 2002, Current Cancer Drug Targets, vol. 2, pp. 55-75, especially p. 58.*
Tamura, et al. "Highly selective and orally active inhibitors of type IV collagenase (MMP-9 and MMP-2): N-Sulfonylamino acid derivatives," 1998, vol. 41, pp. 640-649, especially p. 640.*
Connell, et al. "Patent focus on cancer chemotherapeutics. II Angiogenesis agents: Apr. 2000-Sep. 2000," 2001, vol. 11(1), pp. 77-114, especially p. 84.*
Scozzafava et al., "Protease Inhibitors: Synthesis of Potent Bacterial Collagenase and Matrix Metalloproteinase Inhibitors Incorporating N-4-nitrobenzylsulphonylglycine Hydroxamate Moieties", *J. Med. Chem.*, vol. 43, No. 9, pp. 1858-1865 (2000).
MacPherson et al., "Discovery of CGS 27023A, Non-Peptidic, Potent and Orally Active Stromelysin Inhibitor That Blocks Cartilage Degradation in Rabbits," J. Med. Chem., vol. 40, pp. 2525-2532 (1997).
Tamura et al., "Highly Selective and Orally Active Inhibitors of Type IV Collagenase (MMP-9 and MMP-2): N-Sulfonylamino Acid Derivatives," J. Med. Chem, vol. 41, No. 4, pp. 640-649 (1998).
Uhlenbroek et al., Investigations on Agricultural Fungicides: I. Trichloromethyl thiolsulphonates. Recl. Trav. Chim. PAYS-BAS, vol. 75, pp. 129-146 (1956).

* cited by examiner

*Primary Examiner*—Kamal A. Saeed
*Assistant Examiner*—Susannah L. Chung
(74) *Attorney, Agent, or Firm*—Lydia T. McNally; George R. Dohmann

(57) ABSTRACT

The invention relates to α-amino-N-hydroxy-acetamide derivatives of formula (I), wherein R is di-lower alkyl amino, 1,2,3-triazol-2yl or 1,2,4-triazol-4-yl, m represents an integer from 1 up to and including 10, and n represents an integer from 0 up to and including 10, and salts thereof; to processes for their preparation, pharmaceutical compositions comprising said hydroxamic acid derivatives, the use of such hydroxamic acid derivatives as medicaments, and a method of treating conditions or diseases mediated by matrix-degrading metalloproteinases (MMP's) using said derivatives alone or in combination with one or more other therapeutic agents.

9 Claims, No Drawings

1G(α)-AMINO-N-HYDROXY-ACETAMIDE DERIVATIVES

The invention relates to α-amino acetyl hydroxamic acid derivatives, to processes for their preparation, pharmaceutical compositions comprising said derivatives, the use of the hydroxamic acid derivatives as medicaments, and a method of treating conditions or diseases mediated by matrix-degrading metalloproteinases (MMP's), in particular hyperproliferative diseases, using said derivatives alone or in combination with one or more other therapeutic agents.

The invention relates in particular to α-amino-N-hydroxy-acetamide derivatives of the formula I,

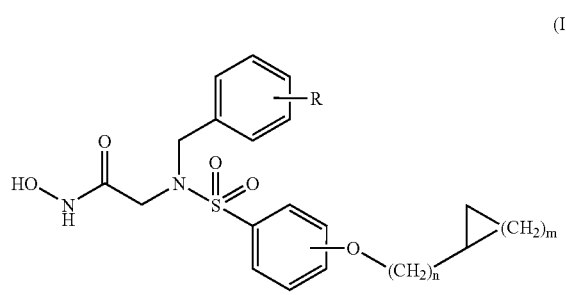

(I)

wherein

R is di-lower alkyl amino, 1,2,3-triazol-1-yl, 1,2,3-triazol-2-yl or 1,2,4-triazol-4-yl, m represents an integer from 1 up to and including 10, and n represents an integer from 0 up to and including 10, or a salt thereof.

Preferably, the group R or the cyclopropylmethoxy group are placed in 4-position of the respective phenyl rings. More preferably, both groups are placed in 4-position of the respective phenyl rings.

In a preferred embodiment of the invention R is dimethylamino or [1,2,3]triazol-2-yl.

n is preferably an integer between 1 and 4, more preferably n is 1.

m is preferably an integer between 1 and 5. More preferably m is 1, 2 or 3 and most preferably m is 1.

Unless stated otherwise, in the present disclosure organic radicals designated "lower" contain not more than 7, preferably not more than 4, carbon atoms.

A lower alkyl group is branched or unbranched and contains 1 to 7 carbon atoms, preferably 1 to 4 carbon atoms, more preferably one or two carbon atoms, and represents for example methyl or ethyl.

Salts are primarily acid addition salts, such as of mineral acids, e.g. hydrochloric acid.

The compounds of formula I have valuable pharmacologically properties. In particular, they are selective inhibitors of MMP's, especially MT1-MMP, MMP-2 and MMP-9, and are useful for the treatment of conditions mediated by MMP's, especially those listed above.

The members of the enzyme family of matrix-degrading metalloproteinases (MMP's), such as gelatinase, stromelysin and collagenase, are implicated in various biological processes, e.g. tissue matrix degradation (e.g. collagen collapse) and in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, psoriasis, as well as HIV-infection (J. Leuk. Biol. 52 (2): 244–248, 1992), artherosclerosis, ventricular dilatation and restenosis in angioplasty.

Macrophage metalloelastase is a further matrix-degrading metalloproteinase which is involved in the degradation of elastin and has been implicated in pathological conditions, e.g. pulmonary disorders such as emphysema and COPD (chronic obstructive pulmonary disease).

Selectivity is generally an advantageous feature of pharmacologically active compounds, because the side-effects of drugs comprising selective compounds are smaller compared with drugs comprising less selective compounds. Since the family of MMP's consists of several different enzymes which are involved in different biological processes, it is desirable to have selective inhibitors of singular MMP's or subgroups of the MMP enzyme family.

The compounds of formula I and their pharmaceutically acceptable salts are particularly useful as MT1-MMP (Membrane-type-1-matrix metalloproteinase), MMP2 (gelatinase A) and MMP9 (gelatinase B) inhibitors.

A number of peptides are reported to interact with biological matter like enzymes, cells or receptors implicated in pathological processes or diseases. Peptides have the disadvantage to get easily hydrolyzed under physiological conditions, especially those physiological conditions to be found in the blood or stomach of warm-blooded animals. The compounds of formula I have the advantage to be no peptides.

Beneficial effects are evaluated in pharmacological tests generally known in the art, and as illustrated herein.

The above-cited properties are demonstrable in in vitro and in vivo tests, using advantageously mammals, e.g. rats, guinea pigs, dogs, rabbits, or isolated organs and tissues, as well as mammalian enzyme preparations. The dosage in vitro may range between about $10^{-5}$ molar and $10^{-10}$ molar concentrations. The dosage in vivo may range, depending on the route of administration, between about 0.1 and 100 mg/kg.

Antiinflammatory activity can be determined in standard inflammation and arthritic animal models well-known in the art, e.g. the adjuvant arthritis model in rats and the collagen II induced arthritis model in mice (Mediators of Inflam. 1, 273–279 (1992)).

One test to determine the inhibition of stromelysin activity is based on its hydrolysis of Substance P using a modified procedure of Harrison et al., Anal. Biochem. 180, 110–113 (1989). In this assay, Substance P is hydrolyzed by recombinant human stromelysin to generate a fragment, Substance P 7-11, which can be quantitated by HPLC. In a typical assay, a 10 mM stock solution of a compound to be tested is diluted in the assay buffer to 50 mM, mixed 1:1 with 8 mg recombinant human stromelysin (mol. wt. 45–47 kDa, 2 Units; where 1 Unit produces 20 mmoles of Substance P 7-11 in 30 minutes) and incubated along with 0.5 mM Substance P in a final volume of 0.125 mL for 30 minutes at 37° C. The reaction is stopped by adding 10 mM EDTA and Substance P 7-11 is quantified on RP-8 HPLC. The $IC_{50}$ for inhibition of stromelysin activity and Ki are calculated from control reaction without the inhibitor.

Macrophage metalloelastase (MME) inhibitory activity can be determined by measuring the inhibition of the degradation of [$^3$H]-elastin by truncated recombinant mouse macrophage metalloelastase as follows:

About 2 ng of recombinant truncated mouse macrophage metalloelastase (FASEB Journal Vol. 8, A151, 1994), purified by Q-Sepharose column chromatography is incubated with test compounds at the desired concentrations in the presence of 5 nM CaCl$_2$, 400 nM NaCl, [$^3$H]elastin (60,000 cpm/tube), and 20 mM Tris, pH 8.0, at 37° C. overnight. The samples are spun in a microfuge centrifuge at 12,000 rpm for 15 minutes. An aliquot of the supernatant is counted in a scintillation counter to quantitate degraded [$^3$H]elastin. IC$_{50}$'s are determined from a range of concentrations of the test compounds and the percent inhibition of enzyme activity obtained.

The inhibitory activities of compounds of formula I on MT1-MMP, MMP1 (collagenase 1) and MMP2 (gelatinase A) can be determined as follows:

Stock solutions of substrate (MCA-Pro-Leu-Gly-Leu-Dpa-Ala-Arg-NH$_2$, C. G. Knight, et al, FEBS lett., 296, 263–266, (1992)), are prepared in 100% DMSO at a concentration 1.0 mM. Stock solutions of inhibitors are prepared in 100% DMSO. The inhibitor is diluted into the assays from a solution in 100% DMSO, and controls substitute an equal volume of DMSO so that the final DMSO concentration from inhibitor and substrate dilutions in all assays is 6.0%. Assays are performed in assay buffer (150 mM NaCl, 10 mM CaCl$_2$, 50 mM Tris-Cl pH 7.5, 0.05% Brij-35) containing 6.0% DMSO once the substrate and inhibitor are diluted into it. The substrate concentration used in the assays is 10 µM. The test is carried out at 37° C. The fluorescence changes are monitored using an excitation wavelength of 320 nm and an emission wavelength of 340 nm. The reaction mixture is added in duplicate to appropriate wells of a 96 well microfluor plate. The reaction mixture is preincubated with the inhibitor for 30 min, the reaction is started by the addition of MMP enzyme and the fluorescence intensity is measured for 10 min. A time point that is on a linear part of the curve is chosen to determine the activity. The inhibition results are expressed as the inhibitor concentrations that produced 50% inhibition (IC$_{50}$) of the activity in the control (non-inhibited) reaction. In this test, the compounds of the formula I and their pharmacologically acceptable salts have an inhibiting concentration IC$_{50}$ [µmol/litre] of 0.0001 and 0.030, usually of 0.0002 to 0.010, for MMP2 and an inhibiting concentration IC$_{50}$ [µmol/litre] of 0.0005 and 0.125, usually of 0.001 to 0.05, for MT1-MMP. Compounds of formula I exhibit an inhibiting concentration IC$_{50}$ for MMP1 (collagenase 1) that is up to 1000-fold higher than the IC$_{50}$ for MT1-MMP, generally it is about 40-fold to 400-fold higher. Compounds of formula I exhibit an inhibiting concentration IC$_{50}$ for MMP1 that is up to 2000-fold higher than the IC$_{50}$ for MMP2, for most compounds of formula I it is about 100-fold to 1000-fold higher.

The enzyme used in the above test are prepared as follows:

MT1-MMP:

Plasmid: The catalytic domain of the cDNA fragment encoding a full length of human MT1-MMP gene [H. Sato et al Nature (London), 370:61–65, 1994)] is amplified by polymerase chain reaction (PCR). The primers used are follows:

CTCCATATGTACGCCATCCAGGGTCTCAA for the sense primer including an NdeI site at the 5'-end for an ATG start codon, and CTCGGATCCTCACCCAT AAAGT-TGCTGGAT-GCC for the antisense primer possessing a BamHI site with one TGA stop codon (1). The resulting PCR product of a 519-bp fragment is subcloned between the NdeI and BamHI unique sites of pET11a (Stratagene). The sequence of catalytic domain of MT1-MMP (CD-MT1-MMP) is verified by the ABI PRISM™ dye terminator cycle sequencing kit with the ABI PRISM™ 377 DNA sequencer (Perkin Elmer).

Expression and Purification: The subcloned CD-MT1-MMP is used to transfect E. coli strain BL21[DE3] (Hanahan, D. J. Mol. Biol. 1983;166(4):557–80) and expressed as insoluble inclusion body materials. Transfectants are grown at 37° C. in 50 ml Luria-Bertani (LB) medium in the presence of 50 g/ml ampicillin to a cell density of OD600=0.6–1.0, and CD-MT1-MMP production is induced with 1 mM isopropyl-1-D-galactopyranoside (IPTG). After treatments with 5 mg/ml lysozyme and 10 µg/ml DNase I, the inclusion bodies are prepared from the harvested cells by using the detergent buffer containing 0.2 M NaCl, 1% w/v deoxycholic acid, and 1% v/v Nonidet P-40. The solubilization is achieved by resuspending the inclusion bodies in the solubilization buffer composed of 6 M urea, 100 mM 2-mercaptoethanol, and 20 mM Tris-Cl, pH 8.5. The enzyme is purified and renaturated using 10 ml of a Q-Sepharose (Amersham Pharmacia Biotech) column equilibrated with 5 mM CaCl$_2$, 0.02% v/v NaN$_3$, in 20 mM Tris-Cl pH 7.5. After washing with three volumes of the same buffer, the bound proteins are eluted with two volumes of a linear gradient of 0.5–1.0 M NaCl. The collected fractions (1 ml each) are dialyzed for 6 h in equilibrated buffer. Superdex G200 column (1×15 cm) (Amersham Pharmacia) is equilibarated in 20 mM Tris-Cl, pH 7.5, 5 mM CaCl$_2$, 0.02% NaN$_3$. The desalted sample is applied to Superdex G200 column and chromatographed at 0.5 ml/min. Fractions of 1 ml are collected and 30 ml aliquots are analyzed by immunoblotting. Fractions showing the highest purity are pooled, concentrated in an Amicon stirred cell with a YM2 membrane and stored at –80° C.

The eluted protein is dialyzed twice against 5 L buffer of 5 mM CaCl$_2$, 0.5 mM ZnSO$_4$, 20 mM Tris-Cl pH 7.5, then concentrated in an Amicon stirred cell with a YM2 membrane. Under these conditions, the recombinant proteins remain soluble and are correctly folded.

MMP1 (Collagenase 1)

Plasmid: The cDNA for human collagenase is generated by PCR of cDNA derived from RNA isolated from human U937 cells (ATCC# CRL-2367). The primers, used to generate this cDNA, are AAGAAGCTTAAGGCCAGTATG-CACAGCTTTCCT and AAGGCGGCCGCACACCT-TCTTTGGACTCACACCA, corresponding to nucleotides 58 to 1526 of the reported cDNA sequence, GenBank accession number X05231. The resulting cDNA fragment is subcloned into Not I site of a mammalian expression vector pBPV-MMT (Matthias, P. et al., J. Mol. Biol. 1986, 187(4): 557–68).

C127 cells (ATCC-mouse mammary tumor cell line) are grown in Dulbecco's Modified Essential Medium supplemented with 10% heat inactivated fetal bovine serum and 1× antibiotic-antimycotic solution at 37° C. in a humidified CO$_2$ incubator. Cells seeded at 8×10$^5$ in 100 mm dishes are transfected using a calcium phosphate precipitation method. 5 h prior to transfection, medium is replaced with fresh medium. Each dish is transfected with 15 µg of the expression vector. Cells ire washed twice with PBS 16–18 h after transfection and are incubated in growth medium for an additional 48 h. Clones are then selected by incubation with the Neomycin related antibiotic G418 at a concentration of 400 µg/ml. Media from selected clones are analyzed for collagenase expression by an enzymatic assay. Expression and Purification: 16 liters of culture medium are concentrated to 1.6 liters and the enzyme is isolated by the procedures described by Wilhelm et al. (Proc. Natl. Acad. Sci. (USA). 1987; 84: 6725–29). The final product is further purified on a Superose G-75 (Pharmacia/LKB, Piscataway, N.J.) gel filtration column equilibrated in the assay buffer containing 0.15 M NaCl. Enzyme is pooled and stored in aliquots at −70° C. Recombinant procollagenase (43–45 kDa) is activated with 1 mM APMA (Aminophenylmercuric acetate, ICN Pharmaceuticals) for 2 h at 37° C., and the APMA is removed by extensive dialysis against the assay buffer containing 0.15M NaCl. The activated enzyme (~36-kDa) is stored frozen at −70° C. until use.

MMP2 (Gelatinase A)

Plasmid: The cDNA for human proMMP2 is supplied by Prof. Motoharu Seiki, Institute of Medical Science, The University of Tokyo. The cDNA encoding a full length on human pro-MMP2 is generated by PCR of cDNA derived from RNA isolated from human HT1080 cells (ATCC# CCL121). The primers to generate this cDNA are GAAT-TCGATGGAGGCGCTAATGGCCCGG and CTCGAGT-CAGCAGCCTAGCCAGTCGGATTTGAT corresponding to full length human pro-MMP2 of the reported cDNA sequence, GenBank accession number J03210. The resulting 2.0 Kb PCR fragment is cloned into EcoR1/Xho 1 site of pFAST BAC 1 vector (pBAC-MMP2) (I. E. Collier et al, J. Biol. Chem., 263:6579–6587, 1988). Expression and Purification: For baculovirus expression of r-proMMP2, pBAC-MMP2 is transformed into DH10BAC competent cells to produce a r-proMMP2 bacmid DNA. The recombinant bacmid DNA is transfected into cultured insect cells (Tn cells) with Cellfectin reagent (Gibco BRL). Recombinant baculovirus are plaque purified to homogeneity and are used to generate high titer stocks of the recombinant baculovirus. Expression of r-proMMP2 is confirmed by gelatin zymography.

Culture fluids of Tn cells infected with baculovirus are centrifuged and filtrated through a 0.22 mm pore size filter to remove cell debris. The recombinant proMMP2 as absorbed to gelatin Sepharose 4B (Pharmacia Biotech) in equilibration buffer of in 25 mM Tris-HCl (pH 7.5), 1 M NaCl, 10 mM $CaCl_2$, 0.05% Briji 35 at 4° C. After washing the beads with equilibration buffer, r-proMMP2 as eluted with equilibration buffer containing 10% DMSO. The enzyme are stored at 4° C. until activation. For assay, the purified proMMP2 is activated with 1 mM APMA for 1 hr at 37° C.

MMP9 (Gelatinase-B)

MMP9 is prepared form the culture medium of THP1 human monocytic leukemia cells treated with TPA. THP1 cells are maintained in a culture of DMEM/F-12 with 10% FCS and stimulated to produce pro-MMP9 with TPA (1 nM) in serum-free medium for 48 h. All purification procedures are carried out at 4° C. The 1 liters of culture medium is concentrated to 100 ml by Centricon (Amicon) and applied to a column (1×8 cm) of gelatin-sepharose (Pharmacia) equilibrated with 50 mM Tris-Cl (pH=8.0), 300 mM NaCl. The fraction containing pro-MMP-9 is eluted with 10% DMSO in 50 mM Tris-Cl (pH=8.0), 300 mM NaCl, then dialyzed against 50 mM Tris-Cl (pH 7.5), 150 mM NaCl. The fraction is concentrated by Centricon and subjected to column chromatography of Sephadex G200 (2×20 cm) equilibrated with 50 mM Tris-Cl (pH=7.5) containing 150 mM NaCl. The purified Pro-MMP9 is stored at −80° C. as a stock and the necessary amount of pro-form is used for activation. Pro-MMP9 is activated with 1 mM aminophenyl mercury acetate (APMA, ICN Pharmaceuticals) in 50 mM Tris-Cl (pH=7.5) containing 150 mM NaCl, 10 mM $CaCl_2$ and 0.05% Brij-35 (MMP Assay Buffer) for 18 h at 37° C., and the APMA is removed by extensive dialysis against MMP Assay Buffer. The activated MMP9 is stored frozen at −80° C. until use.

Assay of MMP9

The activated MMP-9 (82 kDa) is then used to screen compounds. A fluorogenic peptide, 2-N-methylaminobenzoic acid (Nma)-Gly-Pro-Gln-Gly-Leu-Ala-Gly-Gln-Lys-Nε-(2,4-dinitro-phenyl)(Dnp)-$NH_2$ (Peptide Institute, Osaka, Japan) is used as the only substrate in all MMPs assay in this study at 25 μM. Stock solutions of the substrate are prepared in 100% DMSO at a concentration 1.0 mM. Assays are performed in MMP Assay Buffer. The reaction mixture is added in duplicate to appropriate wells of a 96 well microfluor plate and preincubated at 37° for 30 min. The reaction is started by the addition of 0.5 nM of activated MMP9. Stock solutions of each inhibitor are prepared by dissolving in 100% DMSO. Inhibitors are added into the assay mixture from the diluted solution with 100% DMSO prepared from the stock solutions. An equal volume of DMSO is added to controls. The final concentration of DMSO from inhibitor and substrate solutions is 5.0%. The increase of fluorescence is monitored at 460 nm with excitation at 355 nm. A time point on a linear part of the curve is chosen to determine the activity. The inhibition results are expressed as the inhibitor concentration that produce 50% inhibition ($IC_{50}$) of the activity in the control reaction.

The anti-tumor effect of compounds of formula I can also be demonstrated e.g. in vivo in metastasis models using EGFP transfected HT1080 cells measuring the fluorescence intensity of tumor cells metastasized into the lung of nude mice with intravenously injected tumor cells or using B16-F10 melanoma cells measuring lung tumor nodules after i.v. injection of tumor cells into BDF1 mice.

EGFP transfected HT1080: Nude mice are injected in the tail vein a suspension of tumor cells [$2\times10^6$ cells/0.1 ml of PBS (phosphate buffered saline)]. Animals are dosed with compounds p.o. at −1 hr and +5 hrs relative to the time of the cell injection at the first day (day 0). After that the animals are dosed twice a day, firstly at 9–10:30 a.m. and secondly at 5:30–7:00 p.m. Compounds are administered as a suspension in 1% carboxymethyl cellulose (Wako, Japan) at a dose of 60 mg/kg twice a day. The vehicle alone is administered to the control group. On day 17, the lungs ware removed from mice after sacrificing the animals. The removed lung tissues are divided into pieces of approximately 2–3 mm in diameter and then ca. 100 mg of tissues are suspended in 0.2 ml PBS in the microcentrifuge tubes followed by gentle homogenization and centrifugation. The cells are washed 3 times with 1 ml of lysing reagent (150 mM $NH_4Cl$, 0.1 mM EDTA-4 Na, 10 mM $KHCO_3$ pH 7.4) to lysis red blood cells and 2 times with 1 ml of PBS at room temperature. After the final wash, the cells are lysed with 0.5 ml of 1% Triton in PBS. After centrifugation at 15000 rpm for 5 min, 0.23 ml of each supernatants is transferred into the well of a 96-well multi plate. The fluorescence intensity is determined by using fluorescence plate reader (Cytoflour II) at the excitation and emission wavelength of 485 and 530 nm, respectively. The obtained fluorescence is normalized per lung using the wet lung weight.

The B16-F10 melanoma experimental metastasis model is studied following the method of Fidler. Cells are harvested by trypsinization and washed once with serum-containing medium and three times with cold PBS and then kept on ice. Mice are injected in the tail vein with a suspension of tumor cells ($2\times10^5$ cells/0.1 ml of PBS). Animals are dosed with compounds p.o. at −1 hr, +5 hrs, 23 hrs and 29 hrs relative to the time of the cell injection at the first two days (day 0, 1). After that the animals are dosed once a day in the morning. Compounds are administered as a suspension in 1% carboxymethyl cellulose (Wako, Japan) at a dose of 120 mg/kg/dosing. Vehicle alone is administered to the control group. On day 14, the lung of the mice are removed after sacrificing the animals and the numbers of the tumor nodules are counted manually after fixing with Bouin's solution (2% picric acid in destined water: 10% formaldehyde neutral buffer solution:acetic acid=15:5:1).

The antitumor effect of the compounds of the invention can be determined e.g. by measuring the growth of human tumors implanted subcutaneously in Balb/c nude treated mice according to methodology well-known in the art in comparison to placebo treated mice. Illustrative tumors are e.g. estrogen dependent human breast carcinoma BT20 and MCF7, human bladder carcinoma T24, human colon carcinoma Colo 205, human lung adenocarcinoma A549 and human ovarian carcinoma NIH-OVCAR3.

The effect on tumor anglogenesis can be determined e.g. In rats implanted with Walker 256 carcinoma in pellets to stimulate anglogenesis from vessels of the limbus, as described by Galardy et al, Cancer Res. 54, 4715 (1994).

Furthermore, the antitumor and especially the antimetastatic activity of compounds of formula I can also be demonstrated in a sponteanous metastases model, in which rat mammary tumors BN472 are transplanted orthotopically into recipient rats and metastases to lungs and regional lymph nodes are apparent.

Tumor fragments of ca. 25 mm$^3$ are transplanted under the mammary fat pad of female Brown-Norwegian (BN) rats. A compound of formula I is suspended in 1% carboxymethyl cellulose (CMC) in sterile water. The formulations are administered orally at doses of either 30 mg/kg once per day or 15 mg/kg twice per day. Animals in the tumor-bearing control group and the non-tumor-bearing control group (healthy rats) receive vehicle only. Treatment starts after randomization and continues for 4 weeks. Lung metastases are determined after four weeks of treatment by counting the number of lesions visible on the surface of the lungs after fixation in Bouin's fixative. In this model the compounds of formula I at a dose of either 30 mg/kg once per day or 15 mg/kg twice per day produce reductions in the incidence and/or extent of metastases in lungs and regional lymph nodes. The reduction in the median number of lung metastases or weight of regional lymph nodes is between approximately 25% and 70%. For Example, for the compound of Example 3 the median number of lung foci is about 105 for both dosages compared to a median number of about 230 lung foci in the vehicle control group. Based on the increase in body weight and general health, the compounds appear to be well tolerated. Such results clearly indicate that the compounds of formula I are able to reduce the extent and/or magnitude of metastases, e.g. metastases arising from the BN472 rat mammary carcinoma.

The compounds of the formula I inhibit matrix degradation and are therefore very highly suitable for the treatment of diseases which respond to inhibition of the activity of the enzymes MT1-MMP, MMP2 and/or MMP9. Osteoporosis, in particular, can be mentioned here, and also other diseases in whose course bone resorption by osteoclasts play a part, e.g. tumor-induced hypercalcaemia, Paget's Disease or the treatment of bone metastases, and also inflammatory processes in joints and bones and degeneratives processes in cartilaginous tissue. In particular, the compounds of formula I are useful for the treatment of benign or malignant tumours which respond to inhibition of the enzymes MT1-MMP, MMP2 and/or MMP9, e.g breast, lung, bladder, colon, ovarian, brain, and skin cancer by inhibiting tumor growth, tumor metastasis, tumor progression or invasion and/or tumor angiogenesis. They are able to cause tumour regression and to prevent the growth of micrometastases.

Other conditions to be treated with the compounds of the invention include rheumatoid arthritis, osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemia), restenosis after angioplasty, and also vascular ulcerations, ectasia and aneurysms. Further conditions to be treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies such as Landry-Guillain-Barre-Strohl syndrome for motor defects; also tissue ulceration (e.g. epidermal and gastric ulceration), abnormal wound healing and periodental disease. Also endometriosis, septic shock, inflammatory bowel disease, Crohn's disease and especially brain edema can be treated by the compounds of formula I.

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

Certain metalloproteinase inhibitors have been reported to also inhibit the production and release of tumor necrosis factor (TNF), e.g. TNF-α which is an important mediator of inflammation. Thus, compounds of the invention are potential anti-inflammatory agents in mammals.

The effect of the compounds of the invention on atherosclerotic conditions can be evaluated using atherosclerotic plaques from cholesterol-fed rabbits which contain activated matrix metalloproteinases as described by Sukhova et al, Circulation 90, I 404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque rupture.

The effect on vascular aneurysms, e.g. the inhibition of aneurysm formation, can be determined in experimental models such as Apo-E transgenic mice and/or LDL receptor knockout mice. Aneurysm development can be suppressed by the compounds of formula I.

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can be administered in addition especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patients status after tumor regression, or even chemopreventive therapy, for example in patients at risk.

Therapeutic agents for possible combination are especially one or more cytostatic or cytotoxic compounds, for example, a chemotherapeutic agent or several selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, the VEGF receptor tyrosine kinase or the PDGF receptor tyrosine kinase, a cytokine, a negative growth regulator, such as TGF-β or IFN-β, an aromatase inhibitor, an inhibitor of the interaction of an SH2 domain with a phosphorylated protein, antiestrogens, topoisomerase I inhibitors, topoisomerase II inhibitors, microtubule active agents, alkylating agents, antineoplastic antimetabolites, platin compounds, anti-anglogenic compounds, gonadorelin agonists, anti-androgens, bisphosphonates and trastuzumab.

One embodiment of the invention pertains in particular to compounds of formula I, wherein R is di-lower alkyl amino, 1,2,3-triazol-1-yl, 1,2,3-triazol-2-yl or 1,2,4-triazol-4-yl, m is 1, 2, 3, 4 or 5, and n is 0, and to salts thereof.

A further embodiment of the invention pertains in particular to compounds of formula I, wherein R is di-lower alkyl amino, 1,2,3-triazol-1-yl, 1,2,3-triazol-2-yl or 1,2,4-triazol-4-yl, m is 1, 2, 3, 4 or 5, and n is 1, 2, 3 or 4, and to salts thereof.

The invention relates especially to compounds of formula I, wherein R is dimethylamino or 1,2,3-triazol-2-yl, and to pharmaceutically acceptable prodrug derivatives and salts thereof.

In particular, the following compounds are preferred:
2-[(Cyclopropylmethoxy-benzenesulfonyl)-(4-[1,2,3]triazol-2-yl-benzyl)-amino]-N-hydroxy-acetamide,
2-[(Cyclopropylmethoxy-benzenesulfonyl)-(4-[1,2,3]triazol-2-yl-benzyl)-amino]-N-hydroxy-acetamide-hydrochloride salt,
2-[(Cyclopropylmethoxy-benzenesulfonyl)-(4-dimethylaminobenzyl)-amino]-N-hydroxy-acetamide,
2-[(Cyclopropylmethoxy-benzenesulfonyl)-(4-dimethylaminobenzyl)-amino]-N-hydroxy-acetamide-hydrochloride salt,
2-[(Cyclopropylmethoxy-benzenesulfonyl)-(4-[1,2,3]triazol-1-yl-benzyl)-amino]-N-hydroxy-acetamide,
2-[(Cyclopropylmethoxy-benzenesulfonyl)-(4-[1,2,4]triazol-4-yl-benzyl)-amino]-N-hydroxy-acetamide,
2-[(Cyclopropylmethoxy-benzenesulfonyl)-(4-diethylaminobenzyl)-amino]-N-hydroxy-acetamide, and
2-[(Cyclopropylmethoxy-benzenesulfonyl)-(4-diethylaminobenzyl)-amino]-N-hydroxy-acetamide-hydrochloride salt.

The compounds of the formula I salts thereof are prepared by processes known per se, for example, by reacting a carbonic acid of the formula II (II)

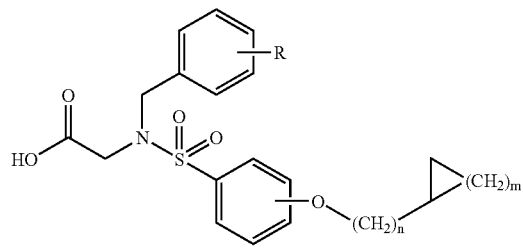

wherein R is di-lower alkyl amino, 1,2,3-triazol-1-yl, 1,2,3-triazol-2-yl or 1,2,4-triazol-4-yl, m represents an integer from 1 up to and including 10, and n represents an integer from 0 up to and including 10, or a salt thereof, first with a reagent which is capable of transforming the carbonic acid into the corresponding acyl halide, optionally in the presence of a suitable catalyst in the presence of a suitable solvent and afterwards with NH$_2$OH in a suitable solvent or mixture of solvents, especially a mixture of water and tetrahydrofurane, and, optionally, for the preparation of a salt, converting a resulting free compound of the formula I into a salt or, if necessary for preparation of a free compound, converting a resulting salt of a compound of the formula I into the free compound.

The above processes are described in more detail below:

The reaction between the carbonic acid of the formula II and the reagent which is capable of transforming the carbonic acid into the corresponding acyl halide can be carried out in suitable solvents, like chloroform or, preferably, dichloromethane. Suitable reagents which are capable of transforming the carbonic acid in the corresponding acyl halide are, e.g. (COCl)$_2$, but also COCl$_2$, SOCl$_2$, POCl$_3$ or POBr$_3$. A suitable catalyst is, e.g., dimethyl-formamide. The reaction is carried out under shaking or stirring. Depending on the nature of the specific reactants the reaction is carried out at a temperature between –10° C. and +50° C., preferably between 0° C. and +30° C. for a period between 30 minutes and 10 hours, preferably between 1 and 3 hours. The further reaction of the preferably freshly prepared acyl halide with NH$_2$OH in a mixture of water and a second solvent which forms a homogeneous solution with the further components, e.g. tetrahydrofurane, is preferably carried out at a temperature between about –35° C. and –5° C., e.g. between –20° C. and –10° C., for about 1 or 2 hours. The reaction is then preferably quenched by pouring the reaction mixture into ice water.

The starting material of the formula II is obtained as follows:

An α-amino acid derivative of formula III (III)

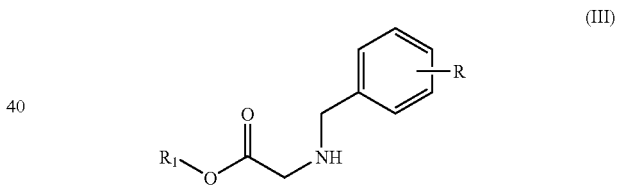

wherein R has the meaning as defined for a compound of formula I and R$_1$ is lower alkyl or benzyl, is reacted with a compound of formula IV (IV)

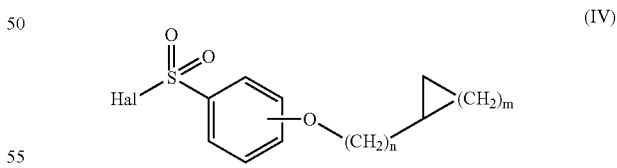

wherein Hal is fluoro, bromo or, preferably, chloro, and m and n have the meanings as defined for a compound of formula I, is reacted in a suitable solvent, like dichloromethane, in the presence of a base, especially a tertiary amine, and, optionally, a catalyst, preferably dimethylaminopyridine, at a temperature between 0° C. and 50° C., e.g. room temperature, for a period between about 30 minutes and 24 hours, for example, 10, 12 or 15 hours, to provide a carbonic acid ester of formula V

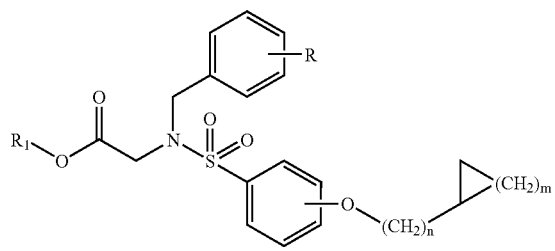

wherein R, m and n have the meanings as defined for a compound of formula I and $R_1$ is lower alkyl or benzyl. The obtained carbonic acid ester can then be hydrolysed to provide the free carbonic acid by methods known as such. Suitable reaction conditions are, e.g., to solve the carbonic acid ester of formula V in tetrahydrofurane and to add lithium hydroxide monohydrate and water successively at a temperature between −10° C. and +10° C., preferably between 0 and +5° C. The reaction mixture is then warmed to room temperature and stirred for about 2 to 12 hours, e.g. 4, 6 or 8 hours.

An α-amino acid derivative of formula III

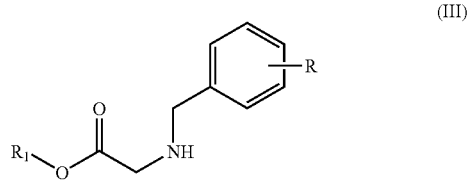

wherein R has the meaning as defined for a compound of formula I and $R_1$ is lower alkyl or benzyl can be obtained, e.g., by reacting an aldehyde of formula VIII

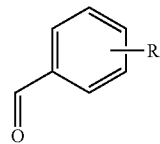

wherein R has the meaning as defined for a compound of formula I in a first step with the hydrochloride salt of an α-amino acid ester of formula IX

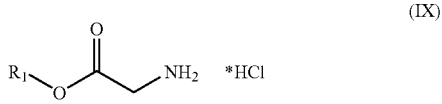

wherein $R_1$ is lower alkyl or benzyl, preferably by adding the ester of formula IX together with a tertiary amine, e.g. triethylamine, and $MgSO_4$ to the aldehyde of formula VIII solved in a suitable solvent, e.g. dichloromethane, in order to prepare the corresponding imine. The imine can then be further reacted with $NaBH_4$ at a temperature below 0° C., preferably between −30° C. and −5° C., more preferably between −20° C. and −10° C., preferably solved in a mixture of tetrahydrofurane and methanol or ethanol, for about 30 to 240 minutes, e.g. 60 or 90 minutes.

An aldehyde of formula VIII wherein R is 1,2,3-triazol-1-yl, 1,2,3-triazol-2-yl or 1,2,4-triazol-4-yl can be obtained by reacting an aldehyde of formula VIII wherein R is chloro, or, very preferably, fluoro, solved in dimethylformamide with 1,2,3-triazole or 1,2,4, triazole in the presence of potassium carbonate at about reflux temperature of the solvent for about 2 to 10 hours, e.g. 4 or 6 hours.

A compound of formula IV wherein Hal is fluoro, bromo or, preferably, chloro, can be obtained by reacting a sulfonic acid sodium salt of formula VI

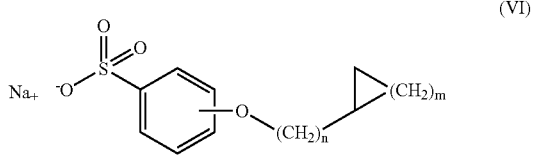

suspended in dichloromethane or another suitable solvent or mixture of solvents, e.g. with $COCl_2$, $SOCl_2$, $POCl_3$ or $POBr_3$, in the presence of catalytic amounts of dimethylformamide at about room temperature for about between 12 and 24 hours.

The sulfonic acid sodium salt of formula VI can be prepared by reacting the compound of formula VII

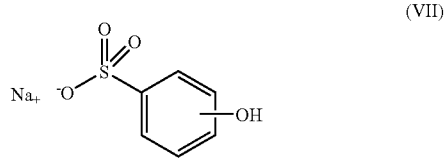

suspended in dimethylformamide and pre-treated with sodium hydride at room temperature with a bromoalkyl-cycloalkane in the presence of catalytic amounts of tetrabutylammonium iodide at a temperature between about 50° C. and 70° C. for 12 to 36 hours, e.g. 24 hours.

General Process Conditions:

Free compounds of the formula I which are obtainable by the process and have salt-forming properties can be converted into their salts in a manner known per se, for example by treatment with acids or suitable derivatives thereof, for example by addition of the acid in question to the compound of the formula I dissolved in a suitable solvent, for example an ether, such as a cyclic ether, in particular dioxane, and especially tetrahydrofurane.

Isomer mixtures obtainable according to the invention can be separated into the individual isomers in a manner known per se, for example by means of fractional crystallization.

The above-mentioned reactions can be carried out under reaction conditions known per se, in the absence or, usually, presence of solvents or diluents, preferably those which are inert towards the reagents used and dissolve these, in the absence or presence of catalysts, condensation agents (for example phosphorus pentoxide) or neutralizing agents, for example bases, in particular nitrogen bases, such as triethylamine, depending on the nature of the reaction and/or of the reaction participants, at a reduced, normal or elevated temperature, for example in the temperature range from about −80° C. to about 200° C., preferably from about −20° C. to about 150° C., for example at the boiling point of the solvent used or at room temperature, under atmospheric pressure or in a closed vessel, if appropriate under pressure, and/or in an inert atmosphere, for example under a nitrogen atmosphere.

The reaction conditions stated specifically in each case are preferred.

Solvents and diluents are, for example, water, alcohols, for example lower alkylhydroxides, such as methanol, ethanol, propanol or, in particular, butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, in particular formic acid or acetic acid, amides of inorganic acids, such as hexamethylphosphoric acid triamide, ethers, for example cyclicethers, such as tetrahydrofurane or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bisalkanesulfines, such as dimethyl sulfoxide, nitrogen-containing heterocyclic compounds, such as pyridine, hydrocarbons, for example lower alkanes, such as heptane, or aromatics, such as benzene, toluene or xylene(s), or mixtures of these solvents, it being possible for the suitable solvents to be chosen in each case for the above-mentioned reactions.

The customary processes are used for working up the compounds of the formula I which can be obtained or their salts, for example solvolysis of excess reagents; recrystallization; chromatography, for example partition, ion or gel chromatography, in particular preparative high pressure liquid chromatography; partition between an inorganic and organic solvent phase; one or several extractions, in particular after acidification or increasing the basicity or the salt content; drying over hygroscopic salts; digestion; filtration; washing; dissolving; evaporation (if necessary in vacuo or under a high vacuum); distillation; crystallization, for example of the resulting compounds in the form of an oil or from the mother liquor, it also being possible for the product to be seeded with a crystal of the end product; or a combination of two or more of the working up steps mentioned, which can also be employed repeatedly.

Starting materials and intermediates can be used in the pure form for example after working up, as mentioned last, in partly purified form or else, for example, directly as a crude product.

As a result of the close relationship between the compounds of the formula I in the free form and in the form of salts, the free compounds and their salts above and below are to be understood appropriately and expediently, where appropriate, as also meaning the corresponding salts or free compounds if the compounds contain salt-forming groups.

The compounds, including their salts, can also be obtained in the form of hydrates, or their crystals can include, for example, the solvent used for the crystallization.

The invention also relates to those embodiment forms of the process in which a compound obtainable as an intermediate at any process stage is used as the starting substance and the missing process steps are carried out, or in which a starting substance is formed under the reaction conditions or is used in the form of a derivative, for example a salt thereof.

Furthermore, the present invention relates to a compound of formula II,

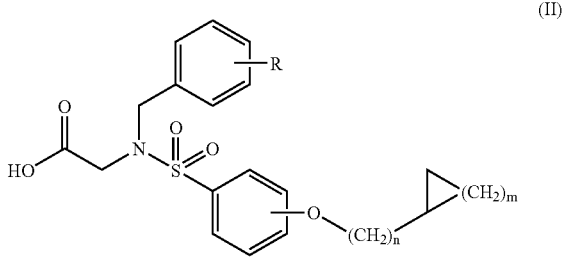

wherein R is di-lower alkyl amino, 1,2,3-triazol-1-yl, 1,2,3-triazol-2-yl or 1,2,4-triazol-4-yl, m represents an integer from 1 up to and including 10, and n represents an integer from 0 up to and including 10, and the salts thereof.

The present invention also relates to methods of using the compounds of the invention and their pharmaceutically acceptable salts, or pharmaceutical compositions thereof, in mammals for inhibiting the matrix-degrading metalloproteinases, e.g. stromelysin (MMP3, MMP10, MMP11), macrophage metalloelastase (MMP12) and, especially, gelatinase (MMP2, MMP9) and MT1-MMP for inhibiting tissue matrix degradation, and for the treatment of matrix-degrading metalloproteinase dependent conditions as described herein, e.g. inflammation, rheumatoid arthritis, osteoarthritis, also tumors (tumor growth, metastasis, progression or invasion), pulmonary disorders (e.g. emphysema), and the like described herein. Tumors (carcinomas) include mammalian breast, lung, bladder, colon, prostate and ovarian cancer, and skin cancer, including melanoma and Kaposi's sarcoma.

Furthermore, the invention relates to a method for treatment of conditions or diseases, especially those described herein, associated with MMP's, especially MT1-MMP, MMP2 and/or MMP9, comprising administering to warm-blooded animals, including humans, in need thereof a therapeutically effective amount of a compound of formula I or of a pharmaceutically acceptable salt or a pharmaceutically acceptable prodrug derivative of such a compound.

The invention relates in particular to a method of treating warm-blooded animals, including humans, suffering from a hyperproliferative disease, especially a tumor disease, and in particular a hyperproliferative disease which responds to inhibition of MT1-MMP, MMP2 and/or MMP9, which method comprises administering an antihyperproliferatively effective amount of a compound of the formula I or of a pharmaceutically acceptable salt or a pharmaceutically acceptable prodrug derivative thereof, or the use of a compound of the formula I for such treatment.

The term "selective MMP2 inhibitor" and "selective MMP9 inhibitor" as used herein means a compound exhibiting an inhibiting concentration $IC_{50}$ for the enzyme MMP1 that is at least 100-fold higher than the inhibiting concentration $IC_{50}$ for the enzyme MMP2 or MMP9, in particular, as determined by the methods described herein. Preferably, the selective MMP2 or MMP9 inhibitor exhibit an inhibiting concentration $IC_{50}$ for the enzyme MMP1 that is at least 1000-fold higher than the $IC_{50}$ for the enzyme MMP2 or MMP9. More preferably, the selective MMP2 or MMP9 inhibitor exhibit an inhibiting concentration $IC_{50}$ for the enzyme MMP1 that is at least 2000-fold higher than the $IC_{50}$ for the enzyme MMP2 or MMP9.

The term "non-peptide" as used herein means a compound without a substructure comprising a chemical bond between an aliphatic amine and a carboxylic acid.

The invention relates also to the use of a compound of formula I or of a pharmaceutically acceptable salt thereof in the inhibition of MT1-MMP, MMP2 and/or MMP9 in warm-blooded animals, including humans, or in the preparation of pharmaceutical compositions for use in the therapeutic treatment of the human or animal body, in particular for the chemotherapy of tumours, COPD, brain edema or asthma Depending on the species, age, individual condition, mode of administration and the particular clinical picture, effective doses, for example daily doses of approximately 0.05 to about 5 g, preferably about 0.25 to about 2 g, of a compound of the present invention are administered to a warm-blooded animal of approximately 70 kg body weight.

The invention relates also to pharmaceutical compositions comprising an effective amount, especially an amount effective in the treatment of one of the above-mentioned disorders, of the active ingredient together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectioning, dissolving or lyophilising processes, and comprise approximately from 1% to 95%, especially from approximately 1% to approximately 20%, active ingredient(s).

Furthermore, the invention relates to a pharmaceutical composition for treatment of tumours in warm-blooded animals, including humans, comprising an antitumourally effective dose of a compound of the formula I as described above or a pharmaceutically acceptable salt or a pharmaceutically acceptable prodrug derivative of such a compound together with a pharmaceutical carrier.

The preparation of prodrug derivatives of hydroxamic acid compounds such as those of formula I is known to the person skilled in the art.

The following Examples serve to illustrate the invention without limiting the scope thereof. Temperatures are given in degrees Centigrade. If not mentioned otherwise, all evaporations are performed under reduced pressure, preferably between about 15 and 100 mmHg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art.

The short names and abbreviations used have the following meanings:

Abbreviations:

| AcOEt | acetic acid ethyl ester |
|---|---|
| CC | column chromatography |
| DMAP | dimethylaminopyridine |
| DMF | dimethylformamide |
| DMSO | dimethylsulfoxide |
| Et | ethyl |
| h | hour(s) |
| Me | methyl |
| min. | minutes |
| NMR | nuclear magnetic resonance |
| r.t. | room temperature |
| sat. | saturated |
| THF | tetrahydrofurane |

Abbreviations for the NMR Spectra Data

| br | broad |
|---|---|
| d | doublet |
| J | coupling constant |
| m | multiplet |
| q | quartet |
| s | singlet |
| t | triplet |
| ppm | parts per million |

EXAMPLE 1

2-[(4-Cyclopropylmethoxy-benzenesulfonyl)-(4-dimethylamino-benzyl)-amino]-N-hydroxy-acetamide To a solution of 36 g (85.2 mmol) of [(4-cyclopropylmethoxy-benzenesulfonyl)-(4-dimethylamino-benzyl)-amino]-acetic acid in 500 ml of $CH_2Cl_2$, 14.8 ml (169.7 mmol) of oxalylchloride followed by 1 ml (12.9 mmol) of DMF are added dropwise (caution!-vigorous gas generation) and stirred for 1 h at 0–5° C. After additional stirring for 1 h at r.t., the obtained acid chloride solution is given slowly into a solution of 157 ml (2379 mmol) of 50% aqueous $NH_2OH$ in 400 ml of THF at −20~−10° C. by using a teflon tube under $N_2$ pressure. After stirring for 1.5 h at −10° C., the reaction mixture is quenched with ice water and precipitated powders are filtered off. The filtrate is extracted with $CH_2Cl_2$, dried over $MgSO_4$ and concentrated under reduced pressure to provide after washing with diethylether the title comppound as a colorless solid; $^1$H-NMR (400 MHz, DMSO-$d_6$): 0.30–0.40 (m, 2H), 0.55–0.65 (m, 2H), 1.20–1.30 (m, 1H), 2.85 (s, 6H), 3.54 (s, 2H), 3.91 (d, 2H, J=6.56 Hz), 4.23 (s, 2H), 6.64 (d, 2H, J=8.04 Hz), 7.00 (d, 2H, J=7.56 Hz), 7.06 (d, 2H, J=8.04 Hz), 7.76 (d, 2H, J=7.56 Hz), 8.82 (brs, 1H), 10.42 (brs, 1H).

Stage 1.1: (4-Dimethylamino-benzylamino)-acetic acid methyl ester

To a solution of 50 g (335 mmol) of 4-aminobenzaldehyde in 1000 ml of $CH_2Cl_2$, 67.3 g (536 mmol) of glycine methylester hydrochloride, 182 ml (1305 mmol) of triethylamine and 70 g of $MgSO_4$ are successively added at 0–5°

C. The mixture is stirred at r.t. for 18 h and filtered through celite. The filtrate is concentrated under reduced pressure and the residue is diluted with AcOEt. Et$_3$N-hydrochloride is filtered off and the filtrate is concentrated under reduced pressure in an azeotropic manner using toluene to give crude imine. To a solution of the crude imine in 500 ml of THF and 500 ml of MeOH, 18 g (475 mmol) of NaBH$_4$ is added portionwise at −20~−10° C. and the mixture is stirred for 1 h. The reaction mixture is slowly quenched with sat. aqueous NH$_4$Cl and then extracted with CH$_2$Cl$_2$. The combined extracts are washed with H$_2$O, brine, dried over MgSO$_4$ and concentrated under reduced pressure. The residue is purified by CC on silica gel (n-Hexane:AcOEt=5:1~1:1) to provide the title compound as pale yellow oil.

Stage 1.2: 4-Cyclopropylmethoxy-benzenesulfonic acid sodium salt

To a suspension of 75 g (323 mmol) of 4-hydroxybenzenesulfonic acid sodium salt in 1350 ml of DMF, 20.67 g (517 mmol) of 60% oil suspended NaH are carefully added portionwise at r.t. To the mixture, 11.93 g (32.3 mmol) of tetrabutylammonium iodide and 50.13 ml (517 mmol) of (bromomethyl)-cyclopropane are added successively. After stirring for 25 h at 60° C., the reaction mixture is cooled to r.t. Precipitates are collected and washed with CH$_2$Cl$_2$ several times, and then recrystalized with mixed solvent (EtOH:H$_2$O=2:1) to give the title compound as a colorless solid.

Stage 1.3: 4-Cyclopropylmethoxy-benzenesulfonyl chloride

To a suspension of 100 g (399.6 mmol) of 4-cyclopropylmethoxy-benzenesulfonic acid sodium salt, 186.55 ml (2557.5 mmol) of thionyl chloride and 6.19 ml (80 mmol) of DMF are added dropwise at r.t. After stirring for 15 h, the mixture is poured into ice water and extracted with CH$_2$Cl$_2$. The combined extracts are washed with H$_2$O, dried over MgSO$_4$ and concentrated under reduced pressure to give the title compound as a colorless solid; $^1$H-NMR (400 MHz, CDCl$_3$): 0.35–0.45 (m, 2H), 0.65–0.75 (m, 2H), 1.25–1.35 (m, 1H), 3.91 (d, 2H, J=7.04 Hz), 7.02 (d, 2H, J=9.04 Hz), 7.96 (d, 2H, J=9.04 Hz).

Stage 1.4: [(4-Cyclopropylmethoxy-benzenesulfonyl)-(4-dimethylamino-benzyl)-amino]-acetic acid methyl ester To a solution of 49.4 g (222 mmol) of [(4-dimethylamino-benzylamino)-acetic acid methyl ester], 41.4 ml (244 mmol) of diisopropylethyl amine and 0.271 g (2.2 mmol) of DMAP in 600 ml of CH$_2$Cl$_2$, 54.8 g (222 mmol) of 4-cyclopropylmethoxy-benzenesulfonyl chloride in 100 ml of CH$_2$Cl$_2$ are added at 0–5° C. After stirring for 15 h at r.t., the reaction mixture is quenched with ice water and sat. aqueous NH$_4$CO$_3$. The mixture is extracted with AcOEt and combined extracts are washed with sat. aqueous NH$_4$CO$_3$ and brine, dried over MgSO$_4$ and concentrated under reduced pressure. The residue is purified by CC on silica gel (n-Hexane: AcOEt=4:1) to give the title compound as a colorless solid.

Stage 1.5: [(4-Cyclopropylmethoxy-benzenesulfonyl)-(4-dimethylamino-benzyl)-amino]-acetic acid To a solution of 74.6 g (172.4 mmol) of the compound of Stage 1.4 in 800 ml of THF, 14.5 g (345.6 mmol) of lithium hydroxide monohydrate and 400 ml of H$_2$O are successively added at 0–5° C. After stirring for 4 h at r.t., the mixture is neutralized with aqueous 2 mol HCl at 0–5° C. and extracted with CH$_2$Cl$_2$ several times. The combined extracts are dried over MgSO$_4$ and concentrated under reduced pressure to give the title compound.

EXAMPLE 2

2-[(4-Cyclopropylmethoxy-benzenesulfonyl)-(4-dimethylamino-benzyl)-amino]-N-hydroxy-acetamide HCl salt To a solution of 50 g (114.3 mmol) of the compound of Example 1 in 500 ml of aqueous 90% CH$_3$CN, 137 ml (137 mmol) of aqueous 1 mol HCl and additional 500 ml of H$_2$O are successively added at r.t. The mixture is lyophilized to give the title compound as a colorless solid; $^1$H-NMR (400 MHz, DMSO-d$_6$): 0.30–0.40 (m, 2H), 0.55–0.65 (m, 2H), 1.20–1.30 (m, 1H), 3.02 (s, 6H), 3.61 (s, 2H), 3.91 (d, 2H, J=7.08 Hz), 4.0 (brs, 1H), 4.33 (s, 2H), 7.07 (d, 2H, J=8.56 Hz), 7.30 (brs, 4 H), 7.76 (d, 2H, J=9.08 Hz), 10.53 (brs, 1H).

EXAMPLE 3

[(4-cyclopropylmethoxy-benzenesulfonyl)-(4-[1,2,3]triazol-2-yl-benzyl)amino]-N-hydroxy-acetamide The title compound is prepared analog to Example 1 starting from [(4-cyclopropyl-methoxy-benzenesulfonyl)-(4-[1,2,3]triazol-2-yl-benzyl)amino]-acetic acid; $^1$H-NMR (400 MHz, CDCl$_3$): 0.32–0.45 (m, 2H), 0.55–0.65 (m, 2H), 1.15–1.30 (m, 1H), 3.66 (s, 3H), 3.90 (d, 2H, J=7.04 Hz), 4.41 (s, 2H), 7.07 (d, 2H, J=8.56 Hz), 7.45 (d, 2H, J=8.56 Hz), 7.79 (d, 2H, J=8.04 Hz), 7.96 (d, 2H, J=8.04 Hz), 8.12 (s, 2H), 8.84 (brs, 1H), 10.49 (brs, 1H).

Stage 3.1: 4-[1,2,3]-Triazol-2-yl-benzaldehyde (A) and 4-[1,2,3]-Triazol-1-yl-benzaldehyde (B)

To a solution of 100 g (803 mmol) of p-fluorobenzaldehyde in 400 ml of DMF, 95 g (1377 mmol) of 1-H-1,2,3-triazole and 200 g (1449 mmol) of K$_2$CO$_3$ are added successively and the mixture is stirred for 4 h at 100° C. The mixture is cooled to r.t. and filtrated through celite. The filtrate is concetrated under reduced pressure to give crude crystals which are washed with AcOEt several times. The solid which is not well soluble in AcOEt is washed with water and dried in vacuo to give 4-[1,2,3]-triazol-1-yl-benzaldehyde (B). The filtrate is concentrated under reduced pressure, the obtained solid is solved in CH$_2$Cl$_2$ and then absorbed on silica gel for dry CC (n-Hexane:AcOEt=2:1~1:2) to provide 4-[1,2,3]-triazol-2-yl-benzaldehyde (A) and further compound (B) as pale yellow solids; $^1$H-NMR (400 MHz, CDCl$_3$): compound A, 7.88 (s, 2H), 8.01 (d, 2H, J=8.56 Hz), 8.29 (d, 2H, J=8.56 Hz), 10.06 (s, 1H); compound B: 7.90 (s, 1H), 7.98 (d, 2H, J=8.56 Hz), 8.07 (d, 2H, J=8.56 Hz), 8.13 (s, 1H), 10.09 (s, 1H).

Stage 3.2: (4-[1,2,3]-Triazol-2-yl-benzylamino)acetic acid methyl ester

To a solution of 60 g (347 mmol) of 4-[1,2,3]-triazol-2-yl-benzaldehyde in 1000 ml of CH$_2$Cl$_2$, 78.9 g (629 mmol) of glycine methylester hydrochloride, 104.2 ml (749 mmol) of triethylamine and 150 g of MgSO$_4$ are successively added at 0–5° C. The mixture is stirred at r.t. for 18 h and filtered through celite. The filtrate is concentrated under reduced pressure and the residue is diluted with AcOEt. Et$_3$N hydrochloride is filtered off and the filtrate is concentrated under reduced pressure in an azeotropic manner using toluene to give the crude imine. To a solution of the crude imine in 600 ml of THF and 600 ml of MeOH, 20 g (526 mmol) of NaBH$_4$ is added portionwise at −20~−10° C. and the mixture is stirred for 1 h. The reaction mixture is slowly quenched with sat. aqueous NH$_4$Cl and then extracted with CH$_2$Cl$_2$. The combined extracts are washed with H₂O, brine, dried over MgSO₄ and concentrated under reduced pressure. The residue is purified by CC on silica gel (n-Hexane:AcOEt=2:1~1:1) to provide the title compound.

Stage 3.3: [(4-Cyclopropylmethoxy-benzenesulfonyl)-(4-[1,2,3]-triazol-2-yl-benzyl)amino]-acetic acid methyl ester To a solution of 79.5 g (323.2 mmol) of the compound of stage 3.2, 80.9 ml (581.6 mmol) of Et₃N and 1.97 g (16.1 mmol) of DMAP in 1000 ml of CH₂Cl₂, a solution of 99.6 g (404 mmol) of 4-cyclopropylmethoxy-benzenesulfonyl chloride in 150 ml of CH₂Cl₂ is added and stirred for 60 min. at 0–5° C. After stirring for additional 18 h at r.t., the reaction mixture is quenched with ice water and extracted with CH₂Cl₂. The combined extracts are washed with H₂O, brine, dried over MgSO₄ and concentrated under reduced pressure. The residue is purified by CC on silica gel (n-Hexane:AcOEt=4:1~2:1) to give the title compound as colorless solid; ¹H-NMR (400 MHz, CDCl₃): 0.35–0.45 (m, 2H), 0.65–0.75 (m, 2H), 1.25–1.35 (m, 1H), 3.58 (s, 3H), 3.87 (d, 2H, J=7.04 Hz), 3.94 (s, 2H), 4.52 (s, 2H), 6.99 (d, 2H, J=7.04 Hz), 7.37 (d, 2H, J=8.56 Hz), 7.81 (s, 2H), 7.82 (d, 2H, J=7.04 Hz), 8.02 (d, 2H, J=8.56 Hz).

Stage 3.4: [(4-Cyclopropylmethoxy-benzenesulfonyl)-(4-[1,2,3]-triazol-2-yl-benzyl) amino]-acetic acid The title compound is obtained analog to Stage 1.5; ¹H-NMR (400 MHz, CDCl₃): 0.35–0.45 (m, 2H), 0.65–0.75 (m, 2H), 1.25–1.35 (m, 1H), 3.86 (d, 2H, J=7.04 Hz), 3.95 (s, 2H), 4.51 (s, 2H), 6.97 (d, 2H, J=8.56 Hz), 7.34 (d, 2H, J=8.56 Hz), 7.80 (s, 2H), 7.83 (d, 2H, J=8.56 Hz), 8.01 (d, 2H, J=8.56 Hz).

Alternatively, the compound of Stage 3.3 can be obtained by the following sequence:

Stage 3.5: (4-[1,2,3]-Triazol-2-yl-phenyl)-methanol

To a solution of 42.26 g (244 mmol) of 4-[1,2,3]-triazol-2-yl-benzaldehyde in 140 ml of THF and 420 ml of MeOH, 9.23 g (244 mmol) of NaBH₄ are added portionwise at 0–5° C. and the mixture is stirred for 30 min. at the same temperature. The reaction is quenched with sat. NH₄Cl at 0–5° C. and the mixture is extracted with AcOEt. The combined extracts are washed with brine, dried over MgSO₄ and concentrated under reduced pressure to give the title compound as a colorless solid.

Stage 3.6: 2-(4-Chloromethyl-phenyl)-2H-[1,2,3]-triazole

To a solution of 50.58 g (289 mmol) of (4-[1,2,3]triazol-2-yl-phenyl)-methanol in 2000 ml of CH₂Cl₂, 31.59 ml (433 mmol) of thionyl chloride is added dropwise at 0–5° C. and the reaction mixture is allowed to warm to r.t. After stirring for 16 h, the reaction mixture is basified with sat. NaHCO₃ at 0–5° C. and extracted with CH₂Cl₂. The combined extracts are washed with brine, dried over MgSO₄ and concentrated under reduced pressure to provide the title compound.

Stage 3.7: (4-Cyclopropylmethoxy-benzenesulfonylamino)-acetic acid methyl ester

To a solution of 7.125 g (56.75 mmol) of glycine methylester hydrochloride in 60 ml of dioxane and 24 ml of H₂O, 15 ml (107.8 mmol) of Et₃N and then a solution of 10 g (40.53 mmol) of 4-cyclopropylmethoxy-benzenesulfonyl chloride in 10 ml of dioxane are added dropwise at 0–5° C. After stirring for 3 h at r.t., the reaction is quenched with ice water and the mixture is extracted with AcOEt. The combined extracts are washed with H₂O, brine, dried over MgSO₄ and concentrated under reduced pressure to give the title compound as a colorless solid; ¹H-NMR (400 MHz, CDCl₃): 0.3–0.40 (m, 2H), 0.65–0.72 (m, 2H), 1.20–1.35 (m, 1H), 3.65 (m, 3H), 3.77 (d, 2H, J=5.04 Hz), 3.86 (d, 2H, J=7.08 Hz), 4.98 (brs, 1H), 6.96 (d, 2H, J=8.52 Hz), 7.77 (d, 2H, J=8.52 Hz).

Stage 3.8: [(4-Cyclopropylmethoxy-benzenesulfonyl)-(4-[1,2,3]triazol-2-yl-benzyl)amino]-acetic acid methyl ester To a solution of 1 g (3.3 mmol) of the compound of Stage 3.7 in 10 ml of DMF, 0.8086 g (4.175 mmol) of 2-(4-chloromethyl-phenyl)-2H-[1,2,3]triazole, 0.0555 g (0.33 mmol) of KI and 0.646 g (4.68 mmol) of K₂CO₃ are added successively at r.t. After stirring for 18 h, the reaction is quenched with ice water and the mixture is extracted with AcOEt. The combined extracts are washed with H₂O, brine, dried over MgSO₄ and concentrated under reduced pressure to give a solid which is washed with diethylether and MeOH to give the title compound.

EXAMPLE 4

According to the methods described under Examples 1 and 3 the following compounds can be obtained:

TABLE 1

| Example | m | n | R |
|---|---|---|---|
| 4a | 1 | 1 | 1,2,4-triazol-1-yl |
| 4b | 1 | 1 | 1,2,3-triazol-1-yl |
| 4c | 1 | 1 | —N(CH₂CH₃)₂ |
| 4d | 1 | 2 | —N(CH₃)₂ |
| 4e | 1 | 3 | —N(CH₃)₂ |
| 4f | 1 | 2 | pyrazol-1-yl |
| 4g | 1 | 3 | pyrazol-1-yl |
| 4h | 2 | 1 | —N(CH₃)₂ |
| 4i | 3 | 1 | —N(CH₃)₂ |
| 4j | 4 | 1 | pyrazol-1-yl |
| 4k | 2 | 3 | —N(CH₃)₂ |

EXAMPLE 5

Dry Capsules 3000 capsules, each of which contain 0.25 g of one of the compounds of the formula I mentioned in the preceding Examples as active ingredient, are prepared as follows:

Composition

| | |
|---|---|
| Active ingredient | 75.00 g |
| Lactose | 750.00 g |
| Avicel PH 102 (microcrystalline cellulose) | 300.00 g |
| Polyplasdone XL (polyvinylpyrrolidone) | 30.00 g |
| Magnesium stearate | 9.00 g |

Preparation process: The active ingredient is passed through a No. 30 hand screen. The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen. Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

EXAMPLE 6

In vitro Activity

The inhibitory activities of the compounds of Example 2 as determined in the in vitro tests described in the present application are given in Tabel 2.

TABLE 2

| Example | MT1-MMP $IC_{50}$ [nM] | MMP1 $IC_{50}$ [nM] | MMP2 $IC_{50}$ [nM] | MMP9 $IC_{50}$ [nM] |
|---|---|---|---|---|
| 2 | 4.67 ± 0.17 | 1770 ± 144 | 3.29 ± 0.49 | 2.57 ± 0.27 |

The $IC_{50}$ values are the mean values±SEM of three independent experiments.

What is claimed is:

1. An α-amino-N-hydroxy-acetamide derivative of the formula I,

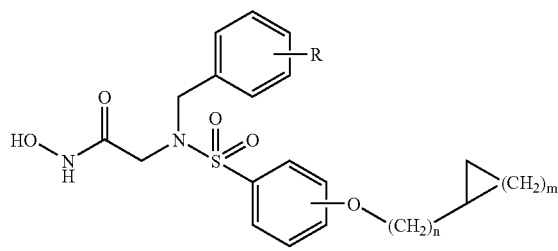

(I)

wherein
R is di-lower alkyl amino,
m is 1, and
n is 1,
or a salt thereof.

2. A compound of formula I according to claim 1, wherein R is dimethylamino or diethylamino,
m is 1, and
n is 1,
or a salt thereof.

3. A compound of formula I according to claim 1, wherein
m is 1, and
n is 1,
or a salt thereof.

4. A compound of the formula I according to claim 1 selected from the group consisting of
2-[(Cyclopropylmethoxy-benzenesulfonyl)-(4-dimethylaminobenzyl)-amino]-N-hydroxy-acetamide,
2-[(Cyclopropylmethoxy-benzenesulfonyl)-(4-dimethylaminobenzyl)-amino]-N-hydroxy-acetamide-hydrochloride salt,
2-[(Cyclopropylmethoxy-benzenesulfonyl)-(4-diethylaminobenzyl)-amino]-N-hydroxy-acetamide, and
2-[(Cyclopropylmethoxy-benzenesulfonyl)-(4-diethylaminobenzyl)-amino]-N-hydroxy-acetamide-hydrochloride salt,
or a salt thereof.

5. A pharmaceutical composition comprising a compound of the formula I according to claim 1 or a pharmaceutically acceptable salt of such a compound together with a pharmaceutical carrier.

6. A method for the treatment of conditions or diseases mediated by MMP's wherein said MMP's is selected from MT1-MMP, MMP-2, or MMP-9, comprising administering to warm-blooded animals, including humans, in need thereof a therapeutically effective amount of a compound of the formula I according to claim 1 or of a pharmaceutically acceptable salt of such a compound wherein said disease is selected from lung, melanoma, breast, colon and ovarian tumors.

7. A compound of the formula I according to claim 1 or a pharmaceutically acceptable salt of such a compound for use in the therapeutic treatment of the human or animal body.

8. A method for treating disease, tumors comprising administering a compound of the formula I according to claim 1 or of a pharmaceutically acceptable salt of such a compound wherein said tumors are selected from lung, melanoma, breast, colon and ovarian tumors.

9. A process for the preparation of an α-amino acetyl hydroxamic acid derivative of the formula I,

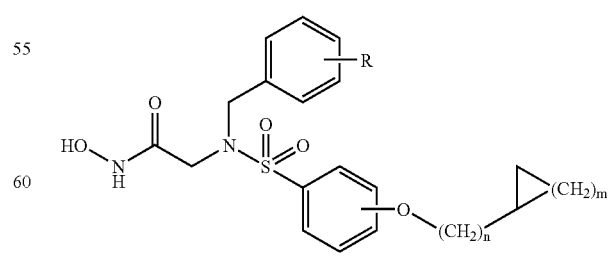

(I)

wherein R is di-lower alkyl amino, m is 1, and n is 1, or a salt thereof, which comprises reacting a carbonic acid of the formula II

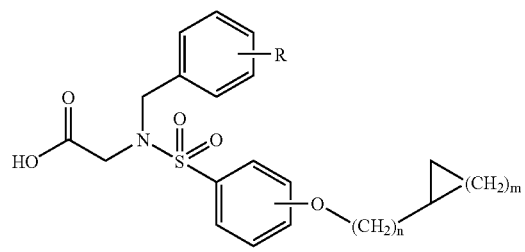
(II)

wherein R, m and n have the meanings as defined for a compound of formula I, first with a reagent which is capable of transforming the carbonic acid into the corresponding acyl halide, optionally in the presence of a suitable catalyst, and then with $NH_2OH$ in a suitable solvent or mixture of solvents, and, optionally, for the preparation of a salt, converting a resulting free compound of the formula I into a salt or, if necessary for preparation of a free compound, converting a resulting salt of a compound of the formula I into the free compound.

* * * * *